(12) United States Patent  (10) Patent No.: US 6,999,816 B2
Van Bentem                      (45) Date of Patent:     Feb. 14, 2006

(54) DETECTING HEART TONES TO IDENTIFY HEART DETERIORATION

(75) Inventor: Maarten Van Bentem, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 353 days.

(21) Appl. No.: 10/422,076

(22) Filed: Apr. 23, 2003

(65) Prior Publication Data

US 2004/0215264 A1 Oct. 28, 2004

(51) Int. Cl.
 *A61N 1/365* (2006.01)

(52) U.S. Cl. .......................... 607/17; 600/528
(58) Field of Classification Search ............ 607/9, 607/17–19, 24, 30, 32, 119, 14, 27, 59–60, 607/62, 122–123; 600/514–515, 528
See application file for complete search history.

(56) References Cited

U.S. PATENT DOCUMENTS

| | | | |
|---|---|---|---|
| 5,700,283 A | * | 12/1997 | Salo ............................ 607/17 |
| 6,810,287 B1 | * | 10/2004 | Zhu et al. ...................... 607/17 |
| 2003/0055352 A1 | | 3/2003 | Hayek et al. |
| 2003/0055461 A1 | | 3/2003 | Girouard et al. |
| 2003/0060723 A1 | | 3/2003 | Joo et al. |
| 2004/0039420 A1 | * | 2/2004 | Jayne et al. ................... 607/5 |

FOREIGN PATENT DOCUMENTS

WO    WO 01/56651 A1    8/2001

\* cited by examiner

*Primary Examiner*—Jeffrey R. Jastrzab
*Assistant Examiner*—Alyssa M Alter
(74) *Attorney, Agent, or Firm*—Daniel G. Chapik; Girma Wolde-Michael (57) ABSTRACT

The invention is directed to an implantable medical device (IMD) that includes an accelerometer. The accelerometer is used to detect heart tones associated with blood flow through one or more cardiac valves. In particular, the IMD measures durations of the heart tones detected by the accelerometer, and uses the measured durations to identify deterioration of the heart. In this manner, the IMD facilitates early detection of cardiac deterioration so that proper therapy can be delivered to the patient to remedy and combat such deterioration.

30 Claims, 5 Drawing Sheets

DETECTING HEART TONES TO IDENTIFY HEART DETERIORATION

FIELD OF THE INVENTION

The invention relates to implantable medical devices, and more particularly to implantable cardiac pacemakers that include diagnostic capabilities.

BACKGROUND OF THE INVENTION

A wide variety of implantable medical devices (IMDs) have been developed in order to monitor patient conditions and deliver therapy to the patient. An implantable pacemaker or cardioverter/defibrillator, for example, typically includes a hermetically sealed housing coupled to one or more leads that are surgically implanted inside a patient for short or long term therapy. The IMD may provide therapeutic stimulation to the patient or may deliver drugs or agents to the patient. Alternatively or additionally, the IMD can have sensing or monitoring capabilities. For example, the IMD may sense information within a patient and store the sensed information for subsequent analysis. Telemetry can be used to communicate sensed information from the IMD to an external medical device so that analysis can be performed. Also, in some cases, the sensed information may be used directly by the IMD to adjust or control the therapy that is delivered to the patient.

IMDs, such as pacemakers, often include an accelerometer for activity level sensing to support rate-responsive pacing. Conventionally, accelerometers are implemented to monitor patient movement and activity. For example, if the accelerometer indicates that the patient is moving, the pacemaker may increase the patient's heart rate to keep up with physiological demands of the body. Similarly, if the accelerometer identifies prolonged non-movement of the patient, the pacemaker can decrease the patient's heart rate.

BRIEF SUMMARY OF THE INVENTION

In general, the invention is directed to an implantable medical device (IMD) that makes use of an accelerometer to detect heart tones associated with blood flow through one or more cardiac valves. In particular, the IMD measures durations of the heart tones detected by the accelerometer, and uses the measured durations to identify deterioration of the heart. For example, if the measured durations exceed a threshold, the IMD may store a value, i.e., a flag, that causes the patient or physician to be alerted during telemetric communication with a programmer. In this manner, early detection of cardiac deterioration can be identified so that proper therapy or surgical intervention can be provided to the patient to remedy and combat such deterioration.

In one embodiment, the invention provides an implantable medical device comprising an accelerometer to detect heart tones associated with blood flow through a cardiac valve, and a heart tone unit to measure durations of the detected heart tones.

In another embodiment, the invention provides a method comprising measuring durations of heart tones associated with blood flow through a cardiac valve of a heart using an accelerometer of an implantable medical device, and identifying a change in the measured durations of the heart tones.

In another embodiment, the invention provides a system comprising a programmer and an implantable medical device that telemetrically communicates with the programmer. The implantable medical device includes an accelerometer to detect heart tones associated with blood flow through a cardiac valve, a heart tone unit to identify an increase in durations of the heart tones relative to a threshold duration, a memory coupled to the heart tone unit, wherein the heart tone unit stores a value in the memory to indicate the increase in the durations of the heart tones relative to the threshold duration, and a telemetry unit to telemetrically communicate information relating to the durations of the heart tones to the programmer when the value is stored in the memory.

In another embodiment, the invention provides an apparatus comprising an accelerometer for measuring durations of heart tones associated with blood flow through a cardiac valve of a heart, and means for identifying a change in the durations of the heart tones.

DETAILED DESCRIPTION OF THE INVENTION

The invention is directed to an implantable medical device (IMD) that includes an accelerometer. The accelerometer is used to detect heart tones associated with blood flow through one or more cardiac valves. Moreover, the accelerometer may also be used for conventional purposes such as detecting patient movement to assess activity level for purposes of rate-responsive pacing. In that case, the invention may be implemented with little modification to the IMD, e.g., using the existing accelerometer and filtering the output to enable heart tone detection associated with blood flow through a cardiac valve in addition to the activity level measurement. In any case, the IMD measures durations of the heart tones detected by the accelerometer, and uses the measured durations to identify deterioration of the heart. Also, amplitudes, frequency content or variations in frequency content can be identified in the detected heart tones in order to improve diagnosis of heart conditions.

For example, if the measured durations exceed a threshold, e.g., a programmable or fixed threshold associated with cardiac deterioration, the IMD may store a value or flag in memory. The stored flag causes an alert to be delivered to the patient or physician during subsequent telemetric communication with a programmer. In this manner, early detection of cardiac deterioration can be identified so that proper therapy or surgical intervention can be delivered to the patient to remedy and combat such deterioration. Alternatively, the IMD may deliver therapy directly, e.g., by delivering drugs or therapeutic pacing pulses to the patient's heart to combat cardiac deterioration once such deterioration is identified. The IMD typically comprises a cardiac pacemaker, but the invention is not limited in that respect. Rather, any IMD could implement an accelerometer for detection of cardiac deterioration in accordance with the invention.

Figure 1:
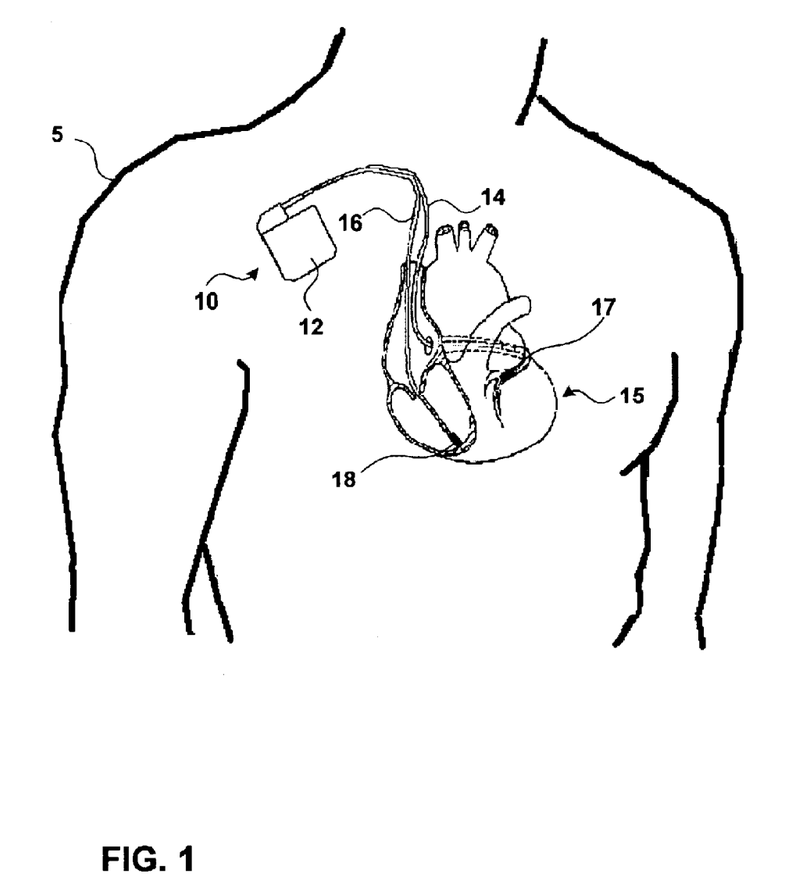
FIG. 1 is a schematic view of a pacemaker that makes use of an accelerometer to identify changes in the durations of the heart tones for identification of deterioration of the patient's heart.

FIG. 1 is a simplified schematic view of pacemaker 10 within a patient's body 5. Pacemaker 10 represents one exemplary embodiment of an IMD according to the invention. Pacemaker 10 includes a hermetically sealed housing 12, and one or more pacing and sensing leads 14 and 16 coupled to housing 12. Leads 14, 16 each position one or more electrodes 17, 18 with respect to heart 15 of patient 5. Electrodes 17, 18 sense electrical signals attendant to the depolarization and repolarization of heart 15, and deliver pacing pulses generated by pacemaker device 10 for causing depolarization of cardiac tissue in the vicinity of the respective electrode 17, 18. Electrodes 17, 18 may comprise unipolar or bipolar electrodes, as are well known in the art. Any number of leads may be used.

Implantable leads 14, 16 may include any number of additional electrodes (not shown) distributed along the length of the respective lead. Electrodes 17, 18 or other electrodes may be used for sensing and/or delivery of stimulation pulses. Additional electrodes (not shown) may also be used for delivery of high voltage defibrillation or cardioversion shocks.

In accordance with the invention, pacemaker 10 includes an accelerometer (not shown in FIG. 1). For example, the accelerometer is typically housed within housing 12. Alternatively, the accelerometer can be disposed along one of leads 14, 16 and implanted at a specific location relative to heart 15. In any case, the accelerometer can be used to detect heart tones associated with blood flow through one or more valves of heart 15. Moreover, pacemaker 10 can identify changes in the durations of the heart tones in order to identify instances of deterioration of heart 15. Specifically, increases in the durations of the heart tones above a threshold may indicate that the cardiac valves are deteriorating. The invention may improve diagnosis and therapy to patient 5 by facilitating early detection of cardiac deterioration.

Figure 2:
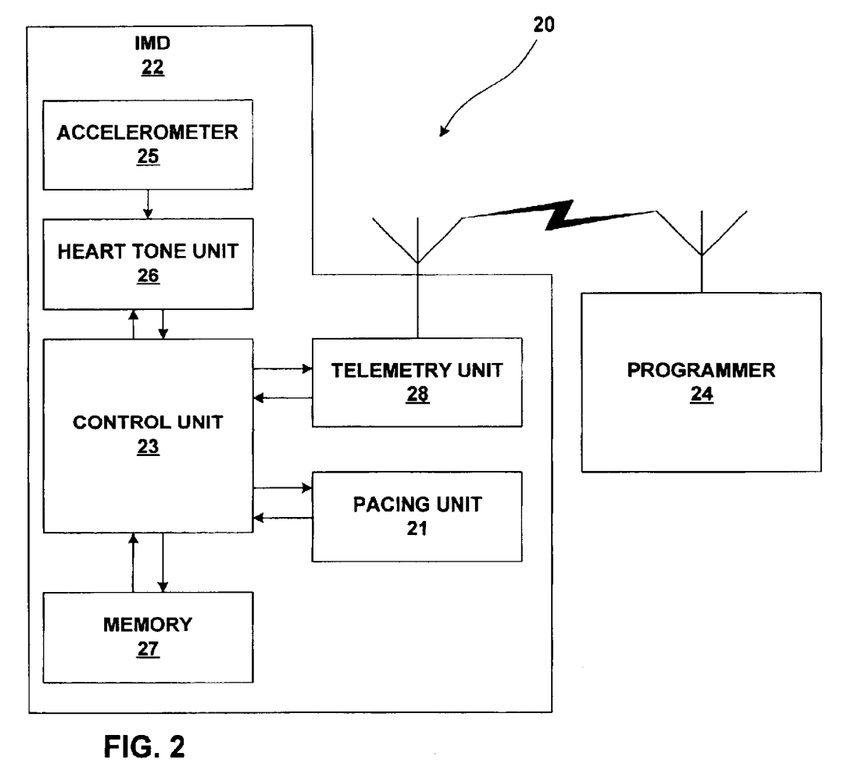
FIG. 2 is an exemplary block diagram of a system that includes an IMD that telemetrically communicates information with a programmer in order to indicate that changes in the durations of the heart tones have been identified by the IMD.

FIG. 2 is an exemplary block diagram of a system 20 which includes an IMD 22 that telemetrically communicates with a programmer 24. IMD 22 may correspond to pacemaker 10 (FIG. 1), or can correspond to any IMD that includes the functionality described herein. As illustrated in FIG. 2, IMD 22 includes an accelerometer 25, a heart tone unit 26, a control unit 23, a memory 27, a pacing unit 21, and a telemetry unit 28.

In accordance with the invention, accelerometer 25 detects heart tones associated with blood flow through a cardiac valve, and heart tone unit 26 measures durations of the heart tones in order to facilitate detection of cardiac deterioration. As used in this disclosure, the phrase "heart tones" refers to heart sounds specifically caused by blood flowing through a cardiac valve. When blood flows through the cardiac valves, the valves flutter, producing sounds which are referred to herein as the heart tones. Sometimes the phrase "heart tones" is also used in medical texts to refer to the sounds associated specifically with closure of cardiac valves, i.e., "flub-lub" sounds produced by closure of cardiac valves. In this disclosure, however, the phrase "heart tones" is reserved specifically to refer to sounds of a fluttering cardiac valve caused by blood flowing through the valve and not flub-lub sounds associated only with valve closure.

Accelerometer 25 may comprise an accelerometer that is also used for monitoring patient movement. In that case, accelerometer 25 would typically operate at approximately 20 Hz. Alternatively, a higher frequency accelerometer could be specifically implemented to improve heart tone detection. In that case, accelerometer 25 may operate at frequencies above 1 KHz, above 2 KHz, and may preferably operate at frequencies of approximately 15 KHz. By way of example, accelerometer 25 may comprise a piezoceramic accelerometer bonded to a hybrid circuit that includes one or more integrated circuits and one or more discrete hardware components. Many other types of accelerometers, however, could also be used in accordance with the invention.

Accelerometer 25 can be implemented inside the housing of IMD 22, i.e., inside the can. Alternatively, accelerometer 25 may be positioned along a lead of IMD 22 for specific positioning at cardiac locations desirable for heart tone detection. Containing the accelerometer 25 inside the housing of IMD 22, however, provides the advantage of electromagnetic shielding and can make operation of accelerometer 25 compatible with magnetic resonance imaging (MRI) techniques, or the like.

Accelerometer 25 detects heart tones associated with blood flow through a cardiac valve, and heart tone unit 26 measures durations of the heart tones in order to facilitate detection of cardiac deterioration. In particular, heart tone unit 26 identifies changes in the durations of the heart tones that may indicate such deterioration. For example, heart tone unit 26 can access one or more stored thresholds that define time durations, that if exceeded, would tend to indicate possible cardiac deterioration. Thus, heart tone unit 26 determines whether the measured durations of the heart tones exceed the threshold duration, and if so, invokes an alert to inform the patient or physician of the potential problem. The thresholds may be programmable or fixed, and are typically stored in memory 27 and accessed by heart tone unit 26 via control unit 23. Moreover, different thresholds may be established for monitoring different cardiac valves or different levels of severity of deterioration of the valves. By way of example, memory 27 may comprise random access memory (RAM), read-only memory (ROM), non-volatile random access memory (NVRAM), electrically erasable programmable read-only memory (EEPROM), flash memory, or the like.

If heart tone unit 26 determines that the measured durations of the heart tones exceed the threshold duration, heart tone unit 26 causes control unit 23 to store a value in memory 27. This stored value can be viewed as a "flag" specifically indicating that potential cardiac deterioration was identified, or may comprise more specific information relating to the measured durations. Control unit 23 coordinates heart tone unit 26 and memory 27, as well as telemetry unit 28 and pacing unit 21. If heart tone unit 26 determines that a flag should be stored in memory, control unit 23 stores the flag in memory 27.

When telemetry unit 28 communicates with programmer 22, control unit 23 accesses memory 27 in order to identify whether information was stored indicating that potential cardiac deterioration was identified. If so, control unit 23 provides the stored information to telemetry unit 28, which communicates the information to programmer 24 relating to the durations of the heart tones.

The communicated information may comprise specific measured values associated with the heart tones, or may simply comprise an indication of the potential problem. In either case, the operator of programmer 24, e.g., typically a physician or the patient, can be alerted to the potential problem of cardiac deterioration. In some cases, a history of heart tone duration may be stored either in IMD 22 or programmer 24. Heart deterioration can be a long-term degenerative disorder, and therefore historical measurements of heart tone duration can provide the physician with useful information for assessing the extent of the problem.

In addition to identifying the durations of heart tones, heart tone unit 26 may also identify other information associated with the heart tones. For example, heart tone unit 26 may process the heart tones to identify amplitudes of the tones, frequency of the tones, time varying frequency of the tones. In each case, heart tone unit 26 may raise a flag if the amplitude, frequency or varying frequency of the tones indicate a potential problem. If so, control unit 23 stores information relating to the detected heart tones in memory 27, and then provides the information from memory 27 to telemetry unit 28 for telemetric communication to programmer 24.

Pacing unit 21 controls the timing of delivery of therapeutic pacing pulses to the patient at the direction of control unit 25. For example, control unit 25 may execute a pacing algorithm and direct pacing 21 to time pacing pulses based on sensed conditions associated with the patient. Pacing unit 21 may include programmable digital counters which control the basic time intervals associated with modes of pacing. Pacer timing unit 21 may also control escape intervals associated with pacing. In some cases, however, IMD 22 does not necessarily include a pacing unit 21, and simply performs passive sensing functions.

Figure 3:
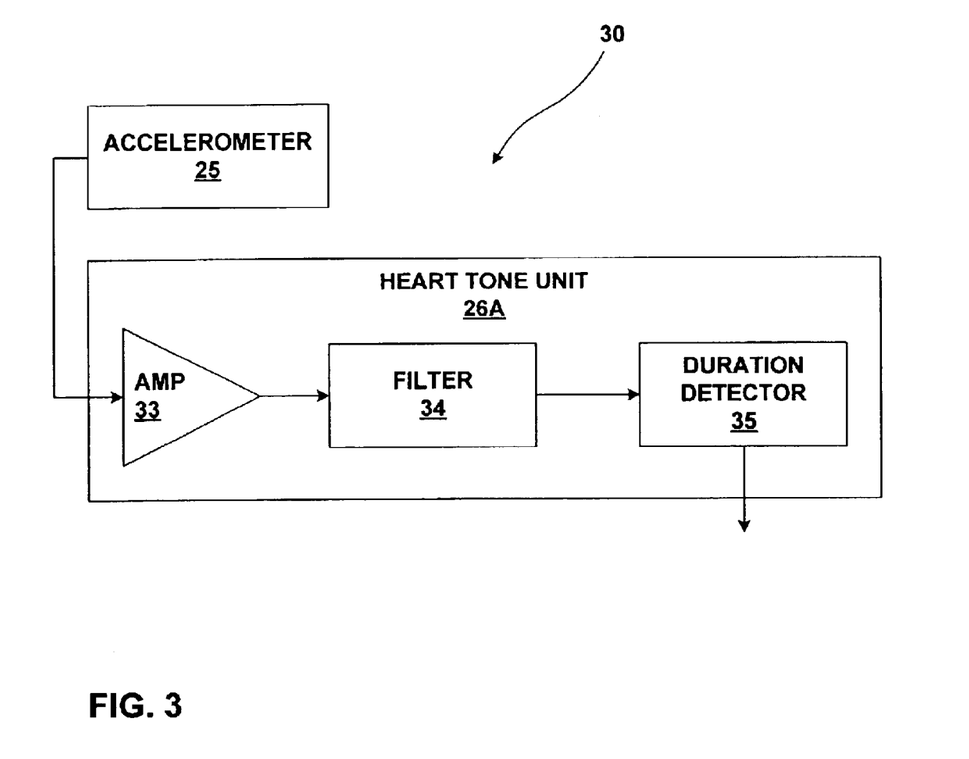
FIG. 3 is a block diagram illustrating components of an IMD according to an embodiment of the invention.

FIG. 3 is another block diagram illustrating components of an IMD 30 according to an embodiment of the invention. In particular, FIG. 3 illustrates accelerometer 25 and heart tone unit 26A, which may correspond to heart tone unit 26 (FIG. 2). In this example, heart tone unit 26A includes an amplifier 33, a filter 34 and a duration detector 35.

Accelerometer 25 detects heart tones associated with blood flow through a cardiac valve. Amplifier 33 amplifies the output of accelerometer 25 and provides input to filter 34. Filter 34 is specifically designed to pass the signals associated with the tones of a specific cardiac valve and to filter out other signals. In some cases, filter 34 may be adjustable or programmable in order to accommodate potential variations between the heart tones of different patients. In that case, a clinician or physician may program or calibrate filter 34 within the clinic improve patient-specific filtering according to the heart tones associated with that patient. Also, additional filters can be implemented for other cardiac valves. In any case, filter 34 filters the output of amplifier 33 to generate a scaled and filtered version of the heart tone initially detected by accelerometer 25.

Duration detector 35 measures the duration of the heart tone. The amplification and filtering provide an adequate signal to enable duration detector 35 to make such measurements. In particular, duration detector 35 can access one or more stored thresholds that define time durations, that if exceeded, would tend to indicate possible cardiac deterioration. Such thresholds may be specifically programmed into duration detector 35 or may be stored in memory (not shown in FIG. 3) and accessed by duration detector 35. In either case, duration detector 35 determines whether the measured durations of the heart tones exceed the threshold duration, and if so, provides output to inform the patient or physician of the potential problem.

For example, if duration detector 35 determines that the measured durations of the heart tones exceed the threshold duration, duration detector 35 may output a value or flag that indicates this fact. The value may be stored in a memory and possibly used by IMD 30 during telemetric communication with a programmer to identify the potential cardiac deterioration problem to a physician or patient. Alternatively, the output of duration detector 35 may be used by IMD 30 directly as feedback in order to adjust the therapy delivered by IMD 30. In that case, IMD 30 may automatically deliver agents, drugs, or therapeutic pulses designed to remedy or treat such cardiac deterioration.

If desired, heart tone unit 26A may also include an amplitude detector (not shown) coupled to filter 34 to detect amplitudes of the tones. Also, heart tone unit 26A may include a frequency detector (not shown) coupled to filter 34 to detect frequencies of the tones, or a time varying frequency detector (not shown) to detect frequency variance of the tones. In each case, the respective detector of heart tone unit 26A may raise a flag if the amplitude, frequency or varying frequency of the tones indicate a potential problem. If so, the respective detector can send signals to control unit 23 (FIG. 2) to cause information relating to the detected heart tones to be stored in memory 27.

Figure 4:
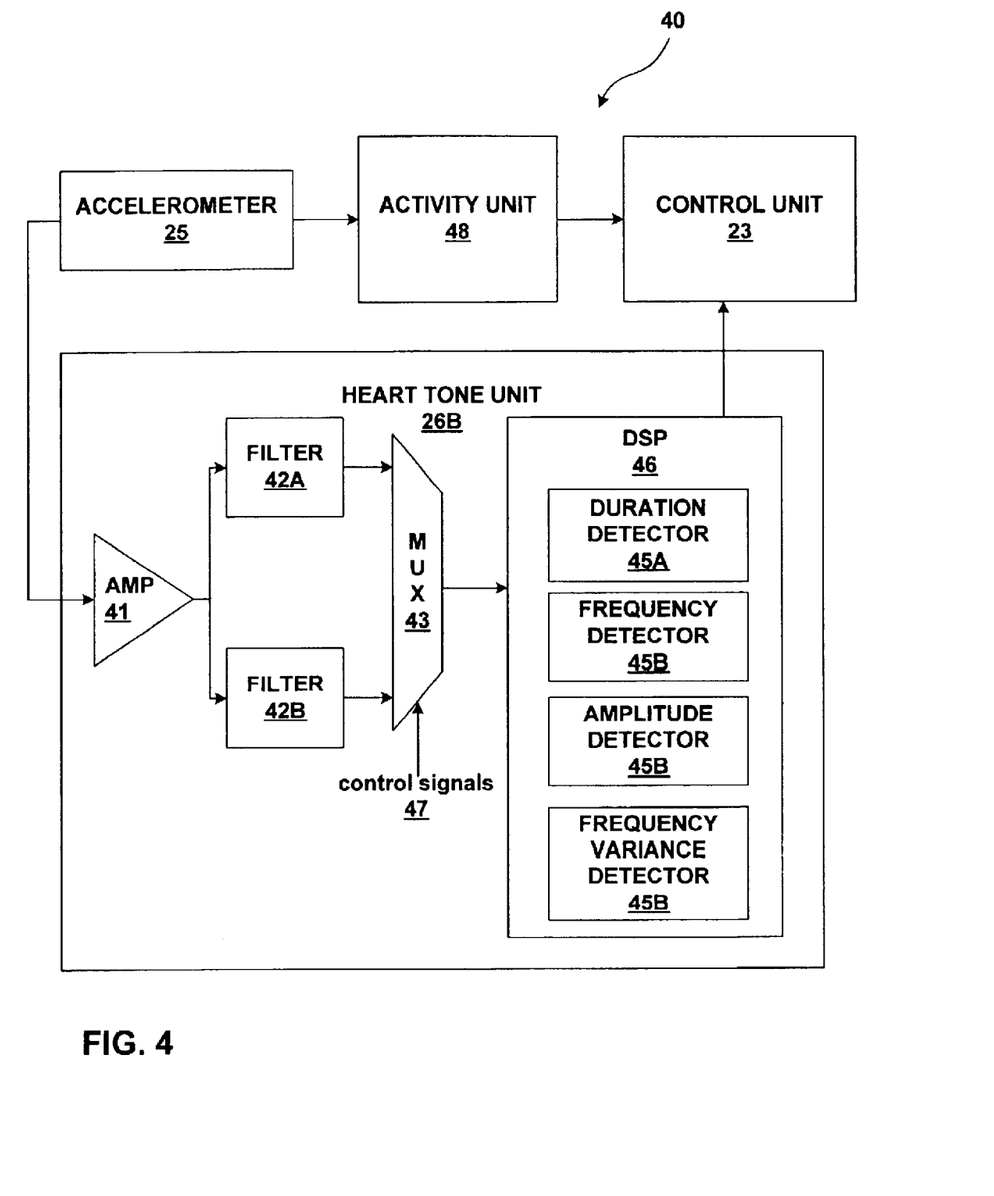
FIG. 4 is another block diagram illustrating components of an IMD according to an embodiment of the invention.

FIG. 4 is another block diagram illustrating components of an IMD 40 according to another embodiment of the invention. In particular, FIG. 4 illustrates accelerometer 25 and heart tone unit 26B, which may correspond to heart tone unit 26 (FIG. 2). In this example, IMD 40 also includes an activity unit 48 that makes use of accelerometer 25 for conventional movement detection.

Accelerometer 25 provides signals to activity unit 48, and activity unit 48 uses the signals to determine whether the patient is moving in a manner that warrants adjustment of the pacing. For example, if the output of accelerometer 25 indicates that the patient is moving, activity unit 48 can send signals to control unit 23 to invoke an increase the patient's heart rate in order to keep up with physiological demands of the body. For example, control unit 23 may send signals to a pacing unit (such as pacing unit 21 illustrated in FIG. 2) to control the rate of delivery of pacing pulses. Similarly, if the output of accelerometer 25 identifies prolonged non-movement of the patient, activity unit 48 can send signals to control unit 23 to decrease the patient's heart rate.

Heart tone unit 26B also takes advantage of accelerometer 25. In particular, heart tone unit 26B measures durations of the heart tones identified by accelerometer 25 in order to facilitate detection of cardiac deterioration. Amplifier 41 amplifies the output of accelerometer 25 and provides input to a plurality of filters 42A, 42B (collectively filters 42). Each of filters 42 are designed to pass the signals associated with tones of a specific cardiac valve and to filter out other signals. In other words, each filter 42 is associated with a different cardiac valve and is specifically designed relative to the tones expected from the given valve when blood flows through the valve. For example, filter 42A may be designed to pass the signals associated with tones of the mitral valve, whereas filter 42B may be designed to pass the signals associated with tones of the tricuspidal valve. Thus, filters 42 can provide a way to distinguish between the tones from the mitral and tricuspidal valves.

In accordance with the invention, any number of filters may be used to monitor any number of valves. In any case, filters 42 filter the output of amplifier 41 to generate a scaled and filtered versions of the heart tone detected by accelerometer 25. In some cases, filters 42 may be adjustable or programmable in order to accommodate potential variations between the heart tones of different patients. Alternatively, the different filters 42 may all be designed to pass the signals associated with tones of a particular valve, but designed slightly differently to accommodate potential variations between the heart tones of different patients.

Multiplexer (MUX) 43 selects output from a given one of filters 42 based on control signals 47 that define which cardiac valve is currently being monitored. The output of MUX 43 is provided to analog-to-digital (A/D) converter 44, which samples and digitizes the scaled and filtered versions of the heart tone detected by accelerometer 25. The digital samples are then provided to digital signal processor (DSP) 46. DSP 46 executes algorithms to identify one or more features of the heart tones.

For example, DSP may include a duration detector 45A to measure the duration of the heart tone. The amplification, filtering and conversion-to-digital provide an adequate signal to enable duration detector 45A to make such measurements. In particular, duration detector 45A can access one or more stored thresholds that define time durations, that if exceeded, would tend to indicate possible cardiac deterioration. Such thresholds may be specifically programmed into duration detector 45A or may be stored in memory (not shown in FIG. 4) and accessed by DSP 46 for use by duration detector 45A. In either case, duration detector 45A determines whether the measured durations of the heart tones exceed the threshold duration, and if so, provides output to inform the patient or physician of the potential problem.

For example, if duration detector 45A determines that the measured durations of the heart tones exceed the threshold duration, duration detector 45A may output a value or flag that indicates this fact. The value may be stored in a memory (not shown in FIG. 4) and possibly used by IMD 40 during telemetric communication with a programmer to identify the potential cardiac deterioration problem to a physician or patient.

If desired, heart tone unit 26B may also include an amplitude detector 45B, a frequency detector 45C, or a time varying frequency detector 45C to respectively detect amplitudes, frequencies or frequency variance of the tones. Separate filters may also be implemented with each respective detector. In other words MUX 43 may select output from respective filters based on what type of detection is being invoked in DSP 46 at any given instance. In each case, the respective detector 45A–45D within DSP 46 of heart tone unit 26B may raise a flag if the duration, amplitude, frequency or varying frequency of the tones indicate a potential problem. If so, the respective detector 45A–45D can send signals to control unit 23 (FIG. 2) to cause information relating to the detected heart tones to be stored in memory 27. In various embodiments, detection and processing of heart tone duration, amplitude, frequency or frequency variance may be used of capture verification, arrhythmia detection or detection of heart deterioration.

DSP 46 may further provide signals to control unit 23 to cause control unit 23 to implement adjustments to the pacing therapy. Alternatively, in other embodiments, DSP 46 can be programmed to identify whether delivery of agents or drugs to the patient could adjust the duration of heart tones in a desirable manner. In that case, a drug delivery unit (not shown) can receive control signals from DSP 46 or control unit 23 to cause automatic delivery of the drugs to the patient to adjust heart tone duration.

Figure 5:
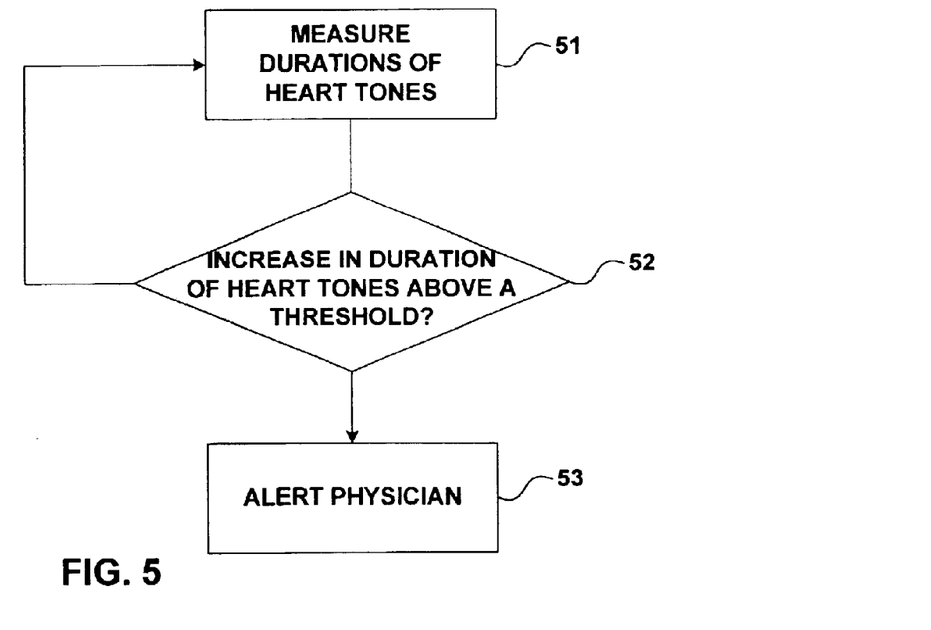
FIGS. 5 and 6 are flow diagrams illustrating processes for identifying heart deterioration in accordance with embodiments of the invention.

FIG. 5 is a flow diagram illustrating a process for identifying heart deterioration in accordance with an embodiment of the invention. As illustrated in FIG. 5, heart tone unit 26 measures durations of heart tones detected by accelerometer 25 (51). If the durations of the heart tones exceed a threshold (yes branch of 52), a physician is alerted (53). For example, at the direction of control unit 23, heart tone unit 26 may cause a flag to be stored in memory 27, which causes telemetry unit 28 to communicate information to programmer 24 indicating the potential cardiac deterioration problem that was identified. In this manner, IMD 22 can improve detection of heart deterioration. If desired, other features of the heart tones can also be detected, such as amplitude, frequency, or frequency variance associated with the heart tones. In each case, the detected information may be identified and communicated to the programmer to alert the physician.

Figure 6:
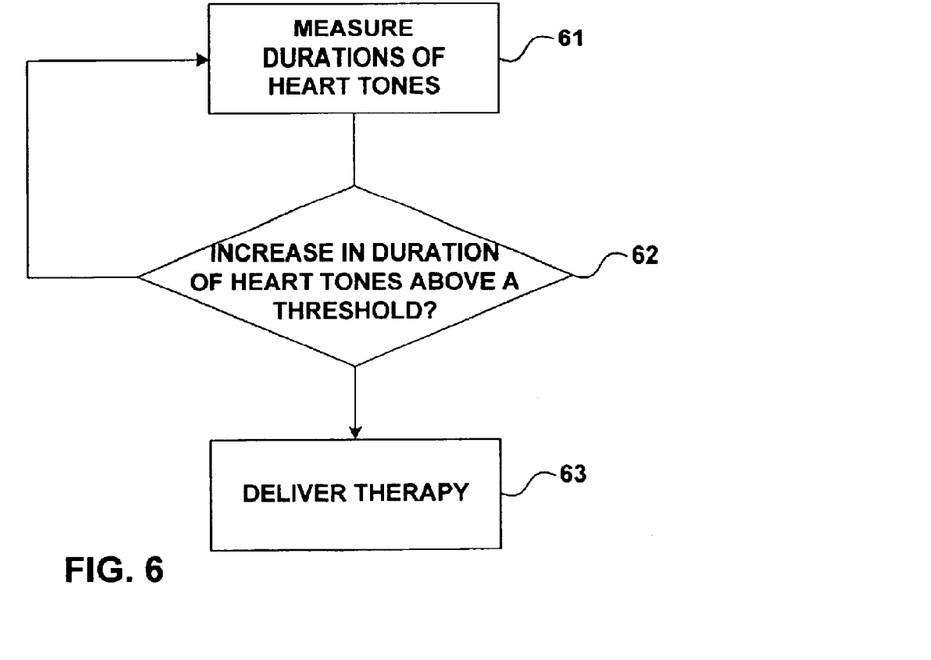

FIG. 6 is another flow diagram illustrating a process for identifying heart deterioration in accordance with an embodiment of the invention. As illustrated in FIG. 6, heart tone unit 26 measures durations of heart tones detected by accelerometer 25 (61). In this example, however, if the durations of the heart tones exceed a threshold (yes branch of 62), IMD 22 delivers therapy to the patient to treat heart deterioration (63). For example, IMD 22 may adjust pacing therapy or may deliver drugs or agents to the patient in order to treat heart deterioration once the durations of the heart tones exceed a threshold. Also, other features of the heart tones can also be detected, such as amplitude, frequency, or frequency variance associated with the heart tones. In those cases, the detected information may be used to automatically adjust therapy to the patient.

A number of embodiments of the invention have been described. However, one skilled in the art will appreciate that the invention can be practiced with embodiments other than those disclosed. For example, although various details of the invention have been provide in the context of a cardiac pacemaker, the same principles may be applied in other IMDs, e.g., that have only sensing capabilities. Also, duration measurements of heart tones may also be used to detect reductions in the durations or a history of duration reductions, e.g., to identify positive effects of therapy. In any case, if the IMD includes an accelerometer, the functionality of the accelerometer can be exploited to monitor heart deterioration.

The various components described herein including heart tone unit 26 (FIG. 2) 26A (FIG. 3) or 26B (FIG. 4) may be implemented in hardware, software, firmware, or the like. Example hardware implementations of such components include implementations within an application specific integrated circuit (ASIC), a field programmable gate array (FPGA), a programmable logic device, specifically designed hardware components, one or more processors, or any combination thereof. If implemented in software, a computer readable medium may store computer readable instructions, e.g., program code, that can be executed by a processor or DSP to carry out one of more of the techniques described above. In other words, duration detector may also be implemented as a DSP that executes software instructions. The disclosed embodiments are presented for purposes of illustration and not limitation, and the invention is limited only by the claims that follow.

What is claimed is:

1. An implantable medical device comprising:
   an accelerometer to detect heart tones associated with blood flow through a cardiac valve; and
   a heart tone unit to measure durations of the detected heart tones.

2. The implantable medical device of claim 1, wherein the heart tone unit identifies a change in the durations of the heart tones.

3. The implantable medical device of claim 1, wherein the heart tone unit identifies an increase in the durations of the heart tones relative to a threshold duration.

4. The implantable medical device of claim 3, further comprising a memory coupled to the heart tone unit, wherein the heart tone unit stores a value in the memory to indicate the increase in the durations of the heart tones relative to the threshold duration.

5. The implantable medical device of claim 4, further comprising a telemetry unit to telemetrically communicate information relating to the durations of the heart tones when the value is stored in the memory.

6. The implantable medical device of claim 1, wherein the heart tone unit includes:
   an amplifier to amplify output of the accelerometer;
   a filter associated with the cardiac valve to filter output of the amplifier; and
   a duration detector to detect the durations based on output of the filter.

7. The implantable medical device of claim 6, further comprising:
   a plurality of filters associated with each of a plurality of cardiac valves; and
   a multiplexer to select output from one of the filters to monitor one of the valves and provide the selected output from one of the filters to the duration detector.

8. The implantable medical device of claim 6, further comprising:
   an analog to digital converter to convert the output of the filter to digital values;
   a digital signal processor to process the digital values; and
   a pacing unit to adjust delivery of pacing pulses by the implantable medical device based on output of the digital signal processor.

9. The implantable medical device of claim 1, wherein the device comprises a pacemaker.

10. The implantable medical device of claim 1, wherein the heart tone unit further measures frequencies associated with the detected heart tones.

11. The implantable medical device of claim 1, wherein the heart tone unit further measures frequency variations associated with the detected heart tones.

12. The implantable medical device of claim 1, wherein the heart tone unit further measures amplitudes associated with the detected heart tones.

13. A method comprising:
   measuring durations of heart tones associated with blood flow through a cardiac valve of a heart using an accelerometer of an implantable medical device; and
   identifying a change in the measured durations of the heart tones.

14. The method of claim 13, wherein identifying the change comprises identifying an increase in the durations of the heart tones.

15. The method of claim 14, further comprising storing a value in the implantable medical device to indicate the increase in the durations of the heart tones.

16. The method of claim 14, wherein identifying the increase in durations comprises comparing the measured durations to a threshold duration and storing a value in the implantable medical device when at least one of the measured durations exceeds the threshold duration.

17. The method of claim 14, further comprising telemetrically communicating to a programmer an indication that the increase in the durations was identified.

18. The method of claim 13, further comprising measuring durations of heart tones associated with blood flow through a plurality of cardiac valves using the accelerometer; and
   identifying an increase in the durations of the heart tones associated with one of the plurality of cardiac valves.

19. The method of claim 13, further comprising delivering therapy to the patient in response to identifying the change in the durations of the heart tones.

20. The method of claim 13, further comprising delivering pacing pulses to the heart.

21. The method of claim 13, further comprising measuring frequencies associated with the heart tones.

22. The method of claim 13, further comprising measuring frequency variations associated with the heart tones.

23. The method of claim 13, further comprising measuring amplitudes associated with the heart tones.

24. A system comprising:
   an implantable medical device programmer; and
   an implantable medical device that telemetrically communicates with the programmer including:
      an accelerometer to detect heart tones associated with blood flow through a cardiac valve;
      a heart tone unit to identify an increase in durations of the heart tones relative to a threshold duration;
      a memory coupled to the heart tone unit, wherein the heart tone unit stores a value in the memory to indicate the increase in the durations of the heart tones relative to the threshold duration; and
      a telemetry unit to telemetrically communicate information relating to the durations of the heart tones to the programmer when the value is stored in the memory.

25. The system of claim 24, wherein the heart tone unit of the implantable medical device includes:
   an amplifier to amplify output of the accelerometer;
   a filter to filter output of the amplifier; and
   a duration detector to detect the durations based on output of the filter.

26. The system of claim 24, wherein the heart tone unit of the implantable medical device further includes:
   a plurality of filters associated with each of a plurality of cardiac valves; and
   a multiplexer to select output from one of the filters based on which of the cardiac valves is being currently monitored and provide the selected output from one of the filters to the duration detector.

27. An apparatus comprising:
   an accelerometer for measuring durations of heart tones associated with blood flow through a cardiac valve of a heart; and
   means for identifying a change in the measured durations of the heart tones.

28. The apparatus of claim 27, further comprising means for identifying an increase in the durations of the heart tones.

29. The apparatus of claim 27, further comprising means for storing a value in an implantable medical device to indicate the change in the durations of the heart tones.

30. The apparatus of claim 27, further comprising means for communicating to a programmer of the implantable medical device an indication that the change in the durations was identified.

* * * * *